United States Patent [19]
Nepon et al.

[11] Patent Number: 5,513,632
[45] Date of Patent: May 7, 1996

[54] VENTILATION OF MEDICAL GASES

[76] Inventors: Mark Nepon, 704 - 388 Portage Avenue, Winnipeg, Manitoba, Canada, R3C 0C8; Rita Korczynski, 1212 - 690 Kenaston Boulevard, Winnipeg, Manitoba, Canada, R3N 1Z3; Ivan Sabesky, 43 Scotia Street, Winnipeg, Manitoba, Canada, R2W 3W6

[21] Appl. No.: 299,525

[22] Filed: Sep. 1, 1994

[51] Int. Cl.⁶ .................................................. A62B 37/00
[52] U.S. Cl. ........................... 128/205.19; 128/200.28; 128/910
[58] Field of Search ................... 128/205.19, 205.12, 128/201.29, 200.28, 910; 433/91, 93

[56] References Cited

U.S. PATENT DOCUMENTS

| | | | |
|---|---|---|---|
| 870,407 | 11/1907 | Anthony | 128/206.28 |
| 3,130,722 | 4/1964 | Dempsey et al. | 128/206.28 |
| 3,625,207 | 12/1971 | Agnew | 128/910 |
| 3,804,086 | 4/1974 | Agnew | 128/202.19 |
| 3,820,536 | 6/1974 | Anspach, Jr. et al. | 128/205.12 |
| 3,877,691 | 4/1975 | Foster . | |
| 4,109,651 | 8/1978 | Steigerwald . | |
| 4,446,861 | 5/1984 | Tada | 128/910 |
| 4,468,825 | 9/1984 | Hobbs | 128/910 |
| 4,807,617 | 2/1989 | Nesti . | |
| 4,840,169 | 10/1989 | Folsom . | |
| 4,848,366 | 7/1989 | Aita et al. | 128/206.28 |
| 4,865,049 | 9/1989 | Gatti . | |
| 4,895,172 | 1/1990 | Lindkvist . | |
| 4,949,714 | 8/1990 | Orr | 128/205.19 |
| 5,127,411 | 7/1992 | Schoolman et al. | 433/91 |
| 5,195,512 | 3/1993 | Rosso . | |
| 5,267,557 | 12/1993 | Her-Mou | 128/206.21 |

OTHER PUBLICATIONS

NIOSH Alert: Request for Assistance in Controlling Exposures to Nitrous Oxide during Anaesthetic Administration [DHHS (NIOSH) 94–100] Apr. 1994.

NIOSH Update DHHS (NIOSH) publication No. 94–118.

McGlothlin et al.; Study protocol: Control of Anaesthetic Gases in Dental Operatories. Cincinatti: National Institute for Occupation Safety and Health, 1988.

Rowland et al.; Reduced Fertility in Dental Assistants, N Engl. J. Med. 1992; 327993–7.

Baird; New England Journal of Medicine editorial 1992; 327:1026–7.

Allander et al.; Thermocamera, a Macroscopic Method for the Study of Pollution with Nitrous Oxide in Operating Theatres. Acta anaesth. scand. 1981, 25, 21–24.

Andersson et al.; A comparison between tracer gas and tracer particle techniques in evaluating the efficiency of ventilation in operating theatres. J.Hyg.Camb (1983) 91.509–519.

Sass–Kortsak et al.; Exposure of Hospital Operating Room to Personnel to Potentially Harmful Environmental Agents. Am.Ind.Hyg Assoc. J. 53(3)–203–209 (1992).

(List continued on next page.)

Primary Examiner—Christopher A. Bennett
Assistant Examiner—William J. Deane, Jr.
Attorney, Agent, or Firm—Murray E. Thrift; Adrian D. Battison

[57] ABSTRACT

A downdraft system is used for withdrawing and collecting medical gases, fumes, mists and particulates from the vicinity of a patient's face. Two intakes are located on respective sides of the patient's face, at the cheeks. The intakes extend from temple to chin. They are connected through a ducting system to a source of vacuum for collecting the medical gases. The ducting system is configured to allow the adjustment of the intake positions. The intakes create a flow of air across the patient's face from above the nose to below the mouth so that gases leaking during administration of gases or exhaled by the patient, and fumes, mists or low velocity particulates generated, for example, in orthodontic procedures are captured in the flow across the patient's face into the intakes. This leaves the patient's mouth and nose fully exposed and unobstructed by the gas evacuation apparatus so that the administration of gases, dental treatments and any other procedures requiring access to the mouth and nose area may be carried out.

8 Claims, 3 Drawing Sheets

OTHER PUBLICATIONS

Tran et al.; Evaluation of Waste Anesthetic Gases, Monitoring Strategies, and Correlations Between Nitrous Oxide Levels and Health Symptoms. Am.Ind Hyg. Assoc.J. 55(1):36–41 (1994).

Berner.; Anasthetic Gases in Operating Rooms. Acta Anaesth.Scand. 1978, 22, 46–54.

Breum et al.; Elimination of Waste Anaesthetic Gases from Theatres. Acta Anaesth. Scand. 1988: 32:388–390.

Mickelsen et al.; Auxiliary Ventilation for the Control of Nitrous Oxide in a Dental Clinic. Appl.Occup.Environ. Hyg.8(6) Jun. 1993.

Davenport et al.; Occupational exposure to anaesthetics in 20 hospitals. Anaesthesia 1980, vol. 35, pp. 354–359.

McIntyre et al.; An Assessment of Operating Room Environment Air Contamination with Nitrous Oxide and Halthane and Some Scavenging Methods. Canad.Anaesth.Soc. J. vol. 25 No. 6 Nov. 1978.

Nillson, et al.; Close Scavenging of Anaesthetic Gases During Mask Anaesthesia. Acta Anaesth. Scand. 1981, 25, 421–426.

McGlothlin, et al.; Control of anesthetic gases in dental operatories. Scan J. Work Environ Helath 1992; 18 Suppl. 2:103–5.

Reiz, et al.; The double mask—a new local scavenging system for anaesthetic gases and volatile agents. Acta Anaesthesiol Scand 1986: 30: 260–265.

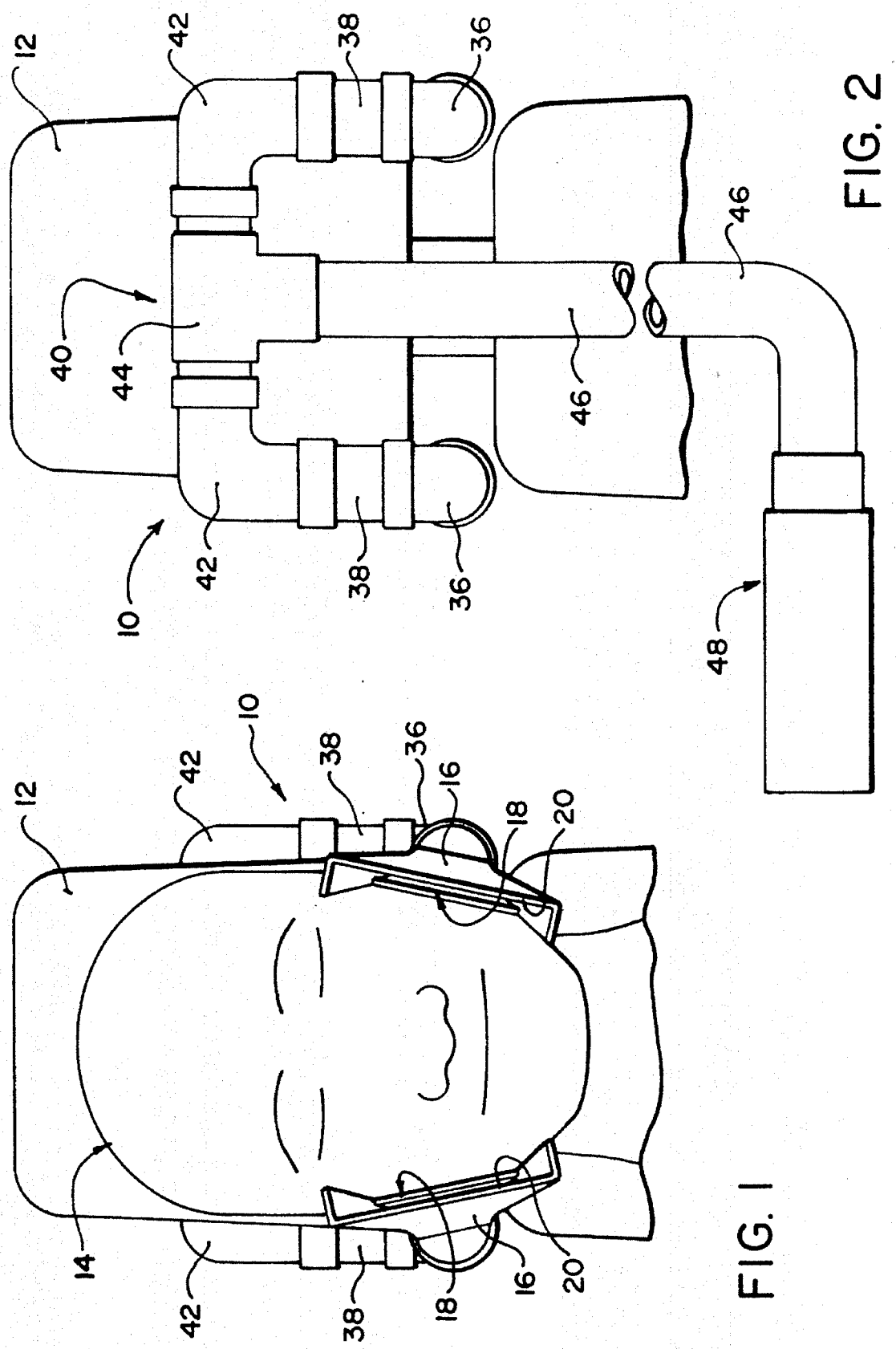

VENTILATION OF MEDICAL GASES

FIELD OF THE INVENTION

The present invention relates to the collection of gases, especially medical gases, and airborne contaminants, for example fumes, mists and particulates, from the vicinity of the face of a patient.

BACKGROUND

In the application of anesthetic or analgesic gases by means of a gas delivery mask to medical and dental patients, gas often escapes into the area around the patient's face and eventually dissipates into a wider area, exposing those in the vicinity to the gas. Studies of this problem are reported in Sass-Kortsak et al.: "Exposure of Hospital Operating Room Personnel to Potentially Harmful Environmental Agents". Am. Ind. Hyg. Assoc. J., Vol. 53, No. 3, March 1992, pp. 203–209 and Tran et al.: "Evaluation of Waste Anesthetic Gases Monitoring Strategies, and Correlations Between Nitrous Oxide Levels and Health Symptoms". Am. Ind. Hyg. Assoc. J., Vol. 55, No. 1, January 1994, pp. 37–41.

Various proposals have been made for dealing with this problem. These include auxiliary ventilation, as reported in Mickelsen et al.: "Auxiliary Ventilation for the Control of Nitrous Oxide in a Dental Clinic". Appl. Occp. Environ. Hyg., Vol 8, No. 6, June 1993, pp. 564–570. That study concluded that air flow rates sufficiently high to cause noise problems or a hood relatively close to the patient would be required for adequate control. Neither high noise levels nor a hood close to a patient's face is acceptable in many, if not most, dental and surgical applications. For example, in dentistry full access to the patient's mouth, without obstruction, is required.

Other proposals are found in the following:

U.S. Pat. No. 5,195,512 issued Mar. 23, 1993, which discloses a suction tube supported in position above the patient's face;

U.S. Pat. No. 4,807,617 issued Feb. 28, 1989, which discloses a mask with a scavenging cup on its outer side;

U.S. Pat. No. 3,877,691 issued Apr. 15, 1975, which discloses a hollow hood or shield, perforated on one side and connected to a suction line;

U.S. Pat. No. 4,895,172 issued Jan. 23, 1990, which discloses a hollow cup that is set over a patient's chin and attached to the patient's head with a harness. Gases are drawn into openings in the front of the cup and thence to a vacuum source.

None of these devices is fully satisfactory. Hoods, shields and masks cover the face at least partially and are not useful in many applications. Suction devices spaced from the face are not exceptionally effective as reported by Mickelsen et al. (supra). A suction arrangement at the chin will not adequately draw in gases leaking from a mask around the nose, because the mask, the hands of a dentist or other obstructions are in the flow path. A chin cup also obstructs access to the mouth for dental and the like treatments.

The present invention is concerned with a method and an apparatus for the effective capturing of these medical gases, and fumes, mists and particulates generated during dental and surgical procedures, while allowing substantially full access to the patient's face, including mouth and nose, for dental treatment, the administration of the gases or substantially any other purpose desired.

SUMMARY

According to the present invention there is provided a method of evacuating gases and airborne contaminants from adjacent the face of a patient, said method comprising creating low pressure areas on opposite sides of the patient's face, beside the patient's cheeks and collecting gases flowing into the low pressure areas.

The low pressure areas are created by placing gas intakes bilaterally at the cheeks of the patient. This withdraws gas across the face and down into the inlets. Gases escaping from any area around a mask or nose cup or from a patient's mouth or nose during exhalation will be captured. The bilateral arrangement ensures that there are no dead zones around the mouth and nose area. The intakes, being at the cheeks, are well clear of the mouth and nose, so that gases may be administered in the usual ways and there will be minimal interference with such things as dental procedures.

According to another aspect of the present invention there is provided an evacuation apparatus for withdrawing gas from adjacent the face of a patient, said apparatus comprising:

two gas intake means;

means for supporting the respective gas intake means on respective opposite sides of the patient's face, at the cheeks; and suction means for drawing gas into the inlet means and collecting the gas so drawn in.

The gas collected will include escaping medical gases as well as ambient air and any airborne contaminants from a location as close as possible to the source from which they are emitted. Medical gases generally are denser than air and will naturally sink in air. The apparatus thus augments the natural flow of these gases when the patient is in the supine position normally adopted for dental and surgical procedures. This contrasts with the withdrawal of gases against their natural flow and from some considerable spacing with overhead suction devices.

The intakes are preferably flat, flaring ducts with open inner sides facing the patient's cheeks, and open front ends facing forwards. The open front ends preferably extend from the temple to the chin of the patient. It has been found that a front end width of 1½ inches (3.8 cm) will draw a sufficient volume of air at a velocity low enough to minimize the noise produced. The intakes may be mounted for adjustment relative to the patient. This may be done by mounting the intakes for rotation on telescopic suction ducts that allow adjustment of the intakes laterally, towards and away from one another. It is also preferred that the intakes are made from a relatively soft material that is at least slightly deformable to allow the intakes to be shaped to conform closely with the patient's face. This reduces the intake of air from locations other than along the patient's cheeks and thus improves efficiency.

In some applications, the apparatus may be installed permanently, for example on a dental chair. In other applications, the apparatus may be portable.

BRIEF DESCRIPTION OF THE DRAWINGS

In the accompanying drawings, which illustrate an exemplary embodiment of the present invention:

FIG. 1 is a front view of an apparatus according to the present invention;

FIG. 1 is a front view of an apparatus according to the present invention;

FIG. 2 is a back view of the apparatus;

DETAILED DESCRIPTION

The terms "front", "back", "top" and "side" are all used relative to a patient's head since the absolute orientation of the apparatus is dependent on the actual orientation of the patient at the time of use.

Figure 3:
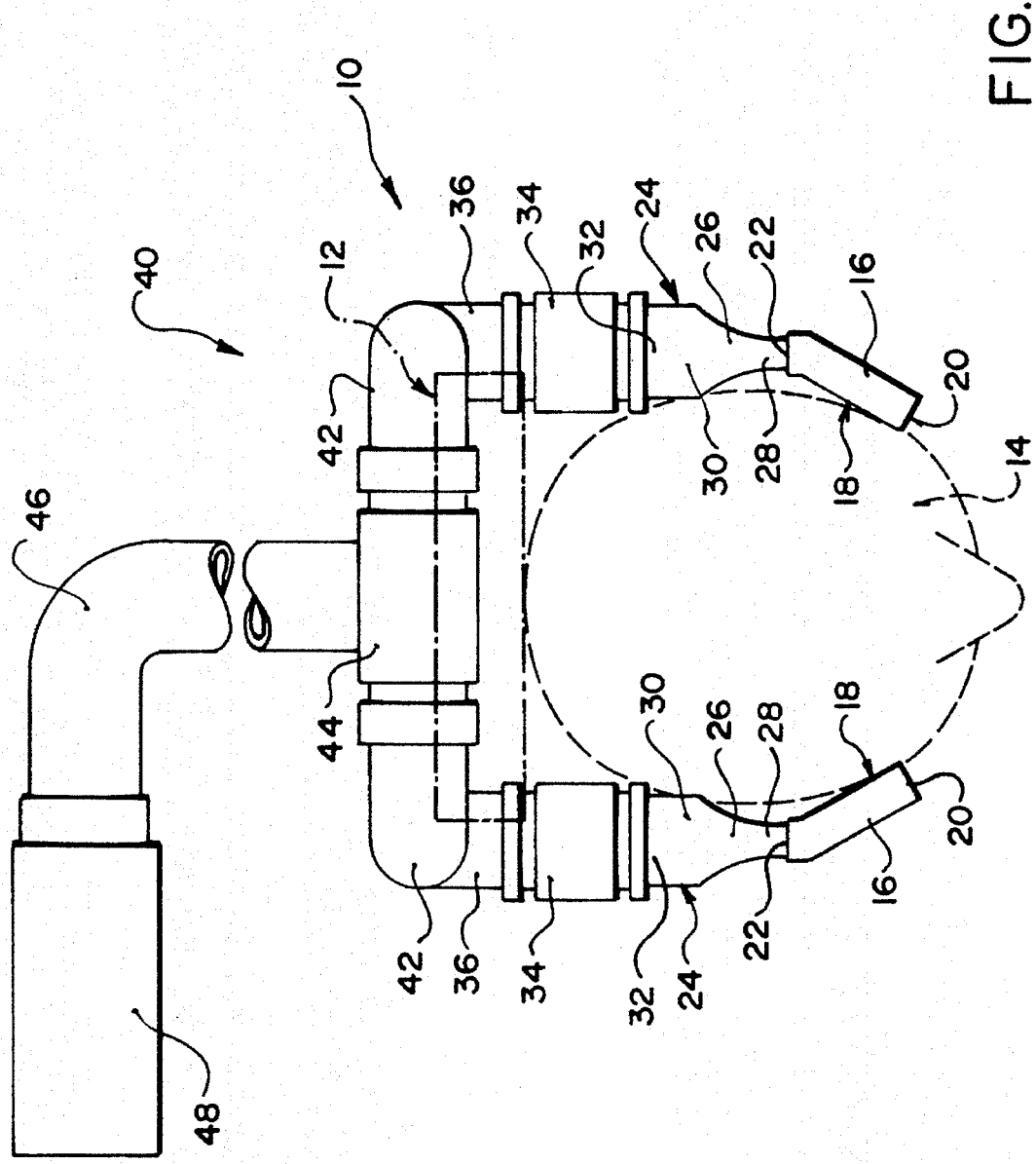
FIG. 3 is a top view of the apparatus.
Figure 4:
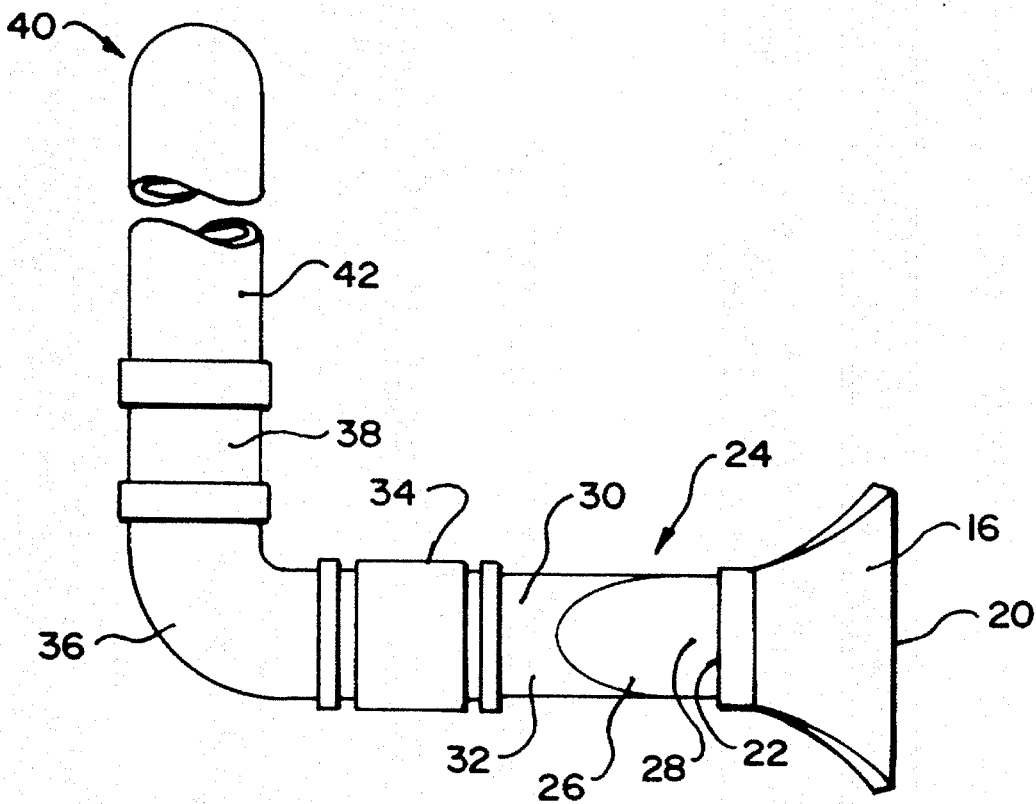
FIG. 4 is a side view of the apparatus.
Figure 5:
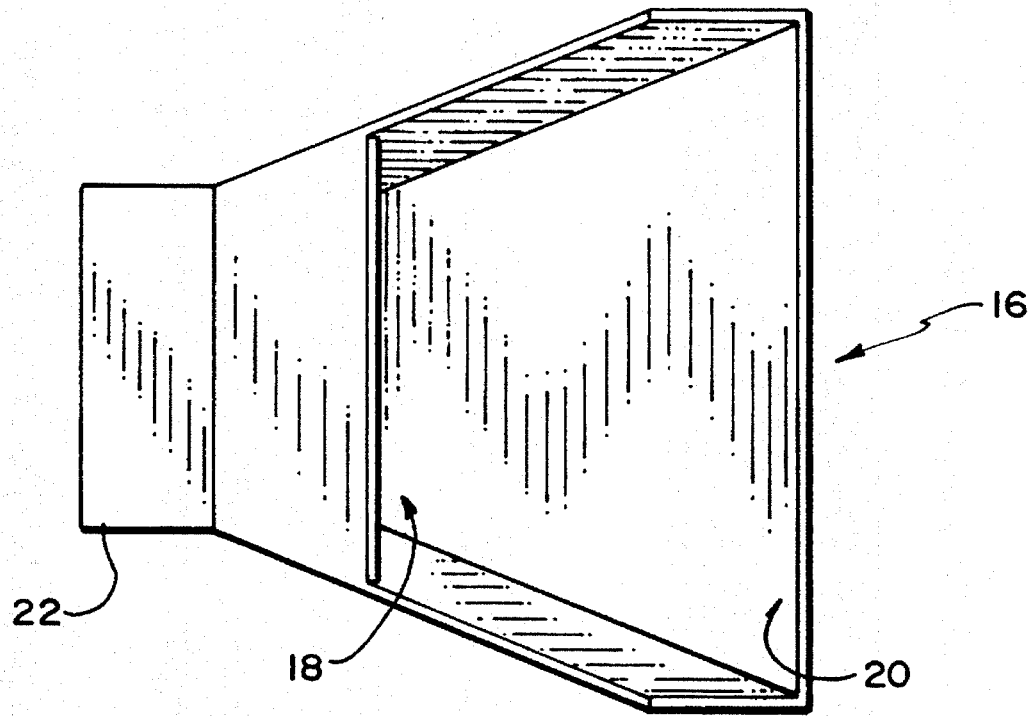
FIG. 5 is an inside view of an intake.

Referring to the accompanying drawings, there is illustrated a gas evacuation apparatus 10 shown associated with the head rest of an existing dental chair 12, partially illustrated in broken lines. FIGS. 1 and 3 of the drawings also show a patient's head 14 associated with the apparatus.

The evacuation apparatus includes two inlet intakes 16 that are, in use, positioned on opposite sides of the patient's head, adjacent the cheeks. Each intake has an open inner side 18 confronting the adjacent cheek of the wearer, an open front end 20 and an opposite exhaust end 22. Each intake is generally rectangular in cross section and flares in height from the exhaust end 22 to the front end 20. The intakes are made from a resilient rubber material that is somewhat deformable so that its shape can be altered to match that of the patient's face.

The exhaust end 22 of each intake is connected to a duct 24. The duct has a transition section 26 with a rectangular section front end 28 connected to the exhaust end 22 of the intake and a circular cross section back end 30. The duct has a rear cylindrical section 32 that slides telescopically, front to back, in an adjustment sleeve 34 so that the fore and aft position of the intake can be adjusted. The cylindrical section 32 also rotates in the sleeve 34 so that the intake can be arranged parallel to the adjacent cheek of a patient.

The adjustment sleeve 34 is connected to an elbow 36 which in turn is connected to an upright duct section 38. The connections of the adjustment sleeve 34 to the intake and the elbow are effected by rubber seals that allow the lateral adjustment of the intake against the face of a patient.

The two duct sections 38 connect to inlets at the opposite ends of a lateral manifold 40. The manifold has a center outlet 44 connected to an exhaust duct 46 leading to a vacuum source 48 that creates a low pressure in the complete evacuation system, thus creating low pressure zones in the intakes, at the patient's cheeks.

In use, the intakes are located on opposite sides of the patient's head, at the cheeks. The intakes are sufficiently wide that the low pressure area in them will create a flow of air across the patient's face from above the nose to the chin and following the contours of the face. Medical gases escaping from a nose cup, a face mask or exhaled by the patient, fumes, mists and particulates will thus be drawn across the patient's face and into the intakes, which are positioned to take advantage of their natural downward flow. The open inner side of the intake effectively uses the patient's face itself as the inner wall of the intake so as to provide a very large intake area and to minimize the opportunity for gas to escape along the patient's face.

With the use of this apparatus, the patient's face is minimally obstructed so that the mouth and nose are accessible for the application of gas in a conventional way or for such other procedures as dental treatment. It has been found that the apparatus is also useful in evacuating the mists, fumes and low velocity particulates generated in surgical and dental procedures.

While one embodiment of the present invention has been described in the foregoing, it is to be understood that other embodiments are possible within the scope of the invention. For example, the illustrated embodiment is shown as attached to a chair such as used in a dental clinic. In other applications, for example in operating theaters, other physical arrangements of the evacuation ducting may be employed. Both permanent and portable installations are possible. The invention is therefore not to be considered limited to the exemplary embodiment described above, but only by the scope of the appended claims.

We claim:

1. A medical gas evacuation apparatus for withdrawing gas and airborne contaminants from adjacent the face of a patient, said apparatus comprising:

two gas intake means, each having an inlet end and an open inner side;

means for supporting the respective gas intake means on respective opposite sides of a patient's face, at the cheeks, with the inlet ends facing forward and extending from temple to chin of the patient and the even inner sides confronting a patient's face; and suction means comprising a duct secured to an exhaust end of the intake, opposite the open end for drawing air and the medical gas into the inlet ends of the intake means and collecting the gas so drawn in.

2. Apparatus according to claim 1 wherein the support means comprise means mounting the intake for selective movement with respect to the patient's face.

3. Apparatus according to claim 2 wherein the support means comprise means mounting the intakes for movement laterally of the patient's face.

4. Apparatus according to claim 3 wherein the support means comprise means mounting each intake for rotation of the intake.

5. Apparatus according to claim 4 wherein the support means comprise means for moving each intake fore and aft beside the patient's head.

6. Apparatus according to claim 1 wherein each intake is generally rectangular in cross section and flares in height from the exhaust end to the open end.

7. Apparatus according to claim 1 wherein each intake is made from a manually deformable material.

8. A medical gas evacuation apparatus for withdrawing gas and airborne Contaminants from adjacent the face of a patient, said apparatus comprising:

gas intake means for drawing air, medical gases and airborne contaminants laterally across a patient's face, from a zone including a patient's mouth and nose, the gas intake means consisting of;

two independent and unconnected gas intakes, each having an elongate inlet opening; and means for supporting the respective gas intakes on respective opposite sides of a patient's face, at the cheeks, with the inlet openings facing forward and extending from temple to chin of the patient without extending across or under the chin; and suction means for drawing air and the medical gas into the inlet openings of the intake means and collecting the gas so drawn in.

* * * * *